United States Patent [19]
Grasmüller et al.

[11] Patent Number: 6,017,133
[45] Date of Patent: Jan. 25, 2000

[54] DEVICE FOR RECOGNIZING THE POSITION OF THE TERMINALS OF COMPONENTS

[75] Inventors: Hans Horst Grasmüller, Mammendorf; Günther Wittmann, München, both of Germany

[73] Assignee: Siemens Aktiengesellschaft, Munich, Germany

[21] Appl. No.: 08/860,515

[22] PCT Filed: Dec. 19, 1995

[86] PCT No.: PCT/DE95/01819

§ 371 Date: Jun. 30, 1997

§ 102(e) Date: Jun. 30, 1997

[87] PCT Pub. No.: WO96/21343

PCT Pub. Date: Jul. 11, 1996

[30] Foreign Application Priority Data

Dec. 30, 1994 [DE] Germany .............................. 44 47 242

[51] Int. Cl.[7] ...................................................... H04N 7/18
[52] U.S. Cl. .......................... 362/252; 362/800; 362/234; 348/131; 382/147; 382/141
[58] Field of Search ..................................... 362/249, 252, 362/227, 800, 234; 382/141, 151, 147; 348/131, 126; 29/833

[56] References Cited

U.S. PATENT DOCUMENTS

| | | | |
|---|---|---|---|
| 4,604,648 | 8/1986 | Kley | 362/249 |
| 4,893,223 | 1/1990 | Arnold | 362/800 |
| 5,060,065 | 10/1991 | Wasserman | 348/131 |
| 5,064,291 | 11/1991 | Reiser | 348/131 |
| 5,822,053 | 10/1998 | Thraikill | 362/800 |

FOREIGN PATENT DOCUMENTS 0 341 806  11/1989  European Pat. Off. .

OTHER PUBLICATIONS

IBM Technical Disclosure Bulletin, vol. 32, No. 8B, Jan. 1990, New York, XP000082202, Lighting Method for Automatic Solder Bond Inspection, pp. 11–12.

*Primary Examiner*—Thomas M. Sember
*Attorney, Agent, or Firm*—Hill & Simpson

[57] ABSTRACT

The device for recognizing the position of the terminals (A) of components (BE) whose optical unwanted structures proceed in two principal directions (X, Y) has an image transducer (BW) equipped with an objective (O); and at least one segmented ring light illumination (RB; RB1, RB2) whose rays (S; S1, S2) are incident onto the surface of the components (BE) from all sides upon exclusion of angular segments (WS) around the principal directions (X, Y). By suppressing the light directions incident perpendicular and parallel to the unwanted structures, the terminals (A) are presented with clearly higher contrast than the other structures of the components (BE). The device is particularly utilized in components vision systems of automatic equipping units. It enables a reliably recognition of the position of the spherical terminals even given flip chips, bare chips and ball grid arrays and, thus, an exact optoelectronic centering of these components.

15 Claims, 3 Drawing Sheets

DEVICE FOR RECOGNIZING THE POSITION OF THE TERMINALS OF COMPONENTS

BACKGROUND OF THE INVENTION

Vision technology is of critical significance for achieving a high equipping precision in the automatic equipping of substrates, particularly printed circuit boards or ceramic substrates, with SMD components for surface mounting (SMD=Surface Mounted Devices). The vision technology thereby comprises a substrate vision system and a components vision system. The substrate vision system acquires reference marks or circuit structures of the substrate with a CCD camera. A computer determines the exact position of the substrate (X, Y, $\phi$) and a potentially existing distortion from the position of the reference marks. For equipping, all equipping positions (X, Y, $\phi$) are correspondingly corrected.

The components vision system is composed of CCD camera, illumination and ground glass screen. The corresponding components vision module is placed on the offering table of the delivery modules. The equipping head places the components onto the ground glass screen such that their terminals can be recognized. The positional deviation of the terminals is determined, for example with a stored pattern, by optoelectronic correlation of all terminals. Using the values of the positional deviations, the automatic equipping unit corrects the equipping paths and the rotational angle to the exact equipping position (X, Y, $\phi$) previously determined with a substrate vision system.

The above-described optoelectronic centering of components with the assistance of a components vision system presents considerable difficulties given some types of component, particularly given flip chips, bare chips and ball grid arrays. When the terminals whose position is to be recognized are viewed as useful structures and all other optically emerging structures of the components are viewed as unwanted structures, the unwanted structures are also at least partially clearly imaged. A reliable image evaluation is made more difficult or entirely prevented as a result thereof. Given, for example, flip chips, the aluminum interconnects, the silicon nitride structures and the silicon oxide structures are to be cited as unwanted structures. The bodies and edges of the components are also to be viewed as unwanted structures.

European reference, A, 0 341 806 has disclosed a means for the inspection of printed circuit boards with SMD components that can be moved across the printed circuit board. The means contains a cylindrical shaft in which two ring light illuminations lying above one another as well as four cameras are arranged. The ring light illuminations are each divided into 4 segments whose middle regions lie in the principal coordinate directions of the printed circuit board proceeding from the center. The cameras are likewise obliquely directed onto the printed circuit board proceeding concentrically from the outside. Their middle axes coincide with the coordinate directions.

The means serves the purpose of checking the presence and position of the components soldered on the printed circuit board. In particular, the means is directed such onto the lateral edges of the component that the ring light segment pointing in this direction and the camera allocated to this are respectively activated. The means likewise serves the purpose of determining the position of solder points on the printed circuit board. This occurs by activating two of the segments lying opposite the solder point and a camera directed perpendicular thereto.

SUMMARY OF THE INVENTION

The invention is based on the problem of creating a device for recognizing the position of the terminals of components wherein the terminals to be recognized are optically isolated and disturbing structure details are optically suppressed for simplification of the image evaluation.

The invention is based on the perception that, given flip chips, bare chips, ball grid arrays and comparable components with spherical terminals, the optical unwanted structures proceed in two principal directions, whereby these principal directions usually coincide with the directions of the component edges. When, during the illumination, the light directions incident parallel and perpendicular to the unwanted structures are suppressed, then the terminals to be recognized in terms of their position are presented with clearly greater contrast than the unwanted structures.

Advantageous developments of the invention are as follows.

The development limits the precluded angle segments of the ring light illumination to ±15°, so that the unwanted structures are imaged clearly more weakly than the useful structures even given greater delivery tolerances of the components. Optimum conditions in view of an optimally intense illumination of the useful structures derive according to claim 3 when the precluded angle segments amount to approximately ±10°.

Given components with highly pronounced unwanted structures, a segmented ring light illumination is especially suitable, the rays thereof being incident onto the surface of the components from all sides at an illumination angle of 45° to 90° relative to the optical axis of the objective. Illumination angles of 55° to 65° are even better for the imaging of the spherical terminals of components with highly pronounced unwanted structures, whereas optimum conditions for the imaging and positional recognition of the terminals derive given an illumination angle of approximately 60°.

The development enables a simple and economic realization of a ring light illumination at a flat angle.

On the basis of a ring light illumination with illumination angles of 15° to 45°, the development enables a high-intensity illumination of the terminals of components with weakly pronounced unwanted structures. Illumination angles of 25° to 35° are even better in this case, whereas optimum conditions for a high-intensity imaging of the terminals of components with weakly pronounced unwanted structures derive given an illumination angle of approximately 30°.

The development enables a simple and economic realization of a ring light illumination at a moderately steep angle.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures of which like reference numerals identify like elements, and in which:

DESCRIPTION OF THE PREFERRED EMBODIMENT

Figure 1:
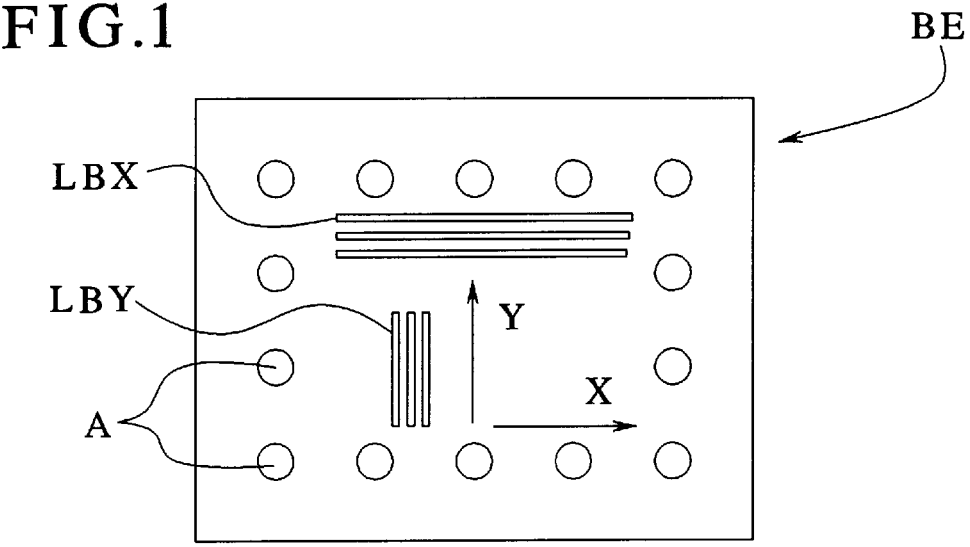
FIG. 1 depicts a component with spherical terminals and optical unwanted structures proceeding in two principal directions, shown in plan view.

In a highly simplified, schematic illustration, FIG. 1 shows a plan view onto a component BE whose spherical terminals arranged in the edge region are referenced A. Two principal directions X and Y proceeding perpendicular to one another and parallel to the component edges are also indicated by arrows. Interconnects LBX proceeding in X-direction and interconnects LBY proceeding in Y-direction, each respectively composed of aluminum, are also indicated in FIG. 1. Given a conventional illumination of the surface of the component BE, these aluminum interconnects LBX and LBY are clearly emphasized, i.e. they disturb a recognition of the position of the terminals a and are thus to be considered optical unwanted structures. The edges of the component BE are also a matter of optical unwanted structures. The body of the component BE is likewise to be viewed as an unwanted structure since its size can vary.

Figure 2:
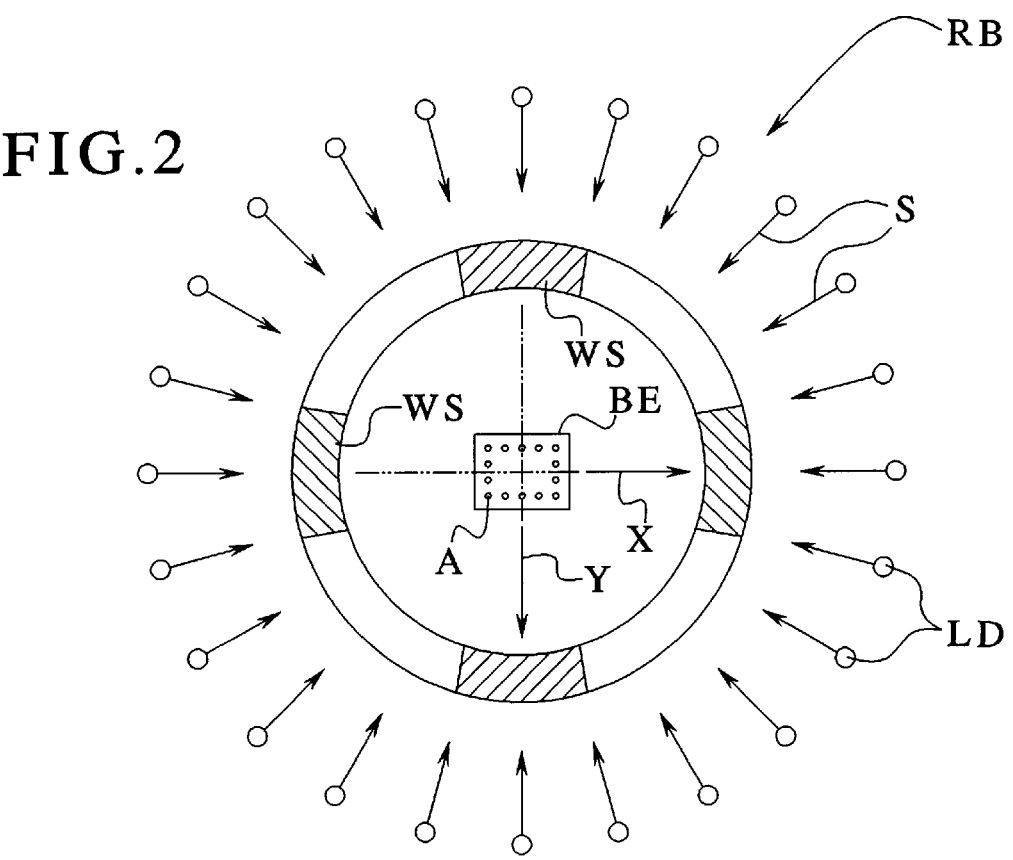
FIG. 2 depicts the schematic diagram of a segmented ring light illumination for the component shown in FIG. 1.

FIG. 2 shows the basic principle of a segmented ring light illumination with which the terminals A of the component BE can be optically isolated and the optical unwanted structures can be at least largely suppressed. The ring light illumination referenced RB comprises a plurality of light-emitting diodes LD arranged on a circle or on a polygon whose rays S would be obliquely incident onto the surface of the component BE arranged in the center from all sides without additional measures. It can be seen, however, that the rays S of the ring light illumination RB are suppressed in the region of angular segments WS around the principal directions X and Y. Delivery tolerances of the components BE are taken into consideration in that it is not only the principal directions X and Y themselves but regions of ±10° around the principal directions X and Y that are excluded from the illumination.

What the angular segments WS effect is that the light directions of the ring light illumination RB incident parallel and perpendicular to the optical unwanted structures are suppressed, and that, asa a result, the terminals A important for an optoelectronic centering of the components BE are presented with clearly higher contrast than the optical unwanted structures.

Given the principle shown in FIG. 2, an incidence of the rays S of the ring light illumination RB onto the surface of the component BE is also suppressed in the region of the principal directions X and Y by the occluding effect of the angular segments WS. According to FIG. 3, the same effect can also be achieved in that the light-emitting diodes are eliminated in the segments of the ring light illumination to correspond to the angular segments WS.

Figure 4:
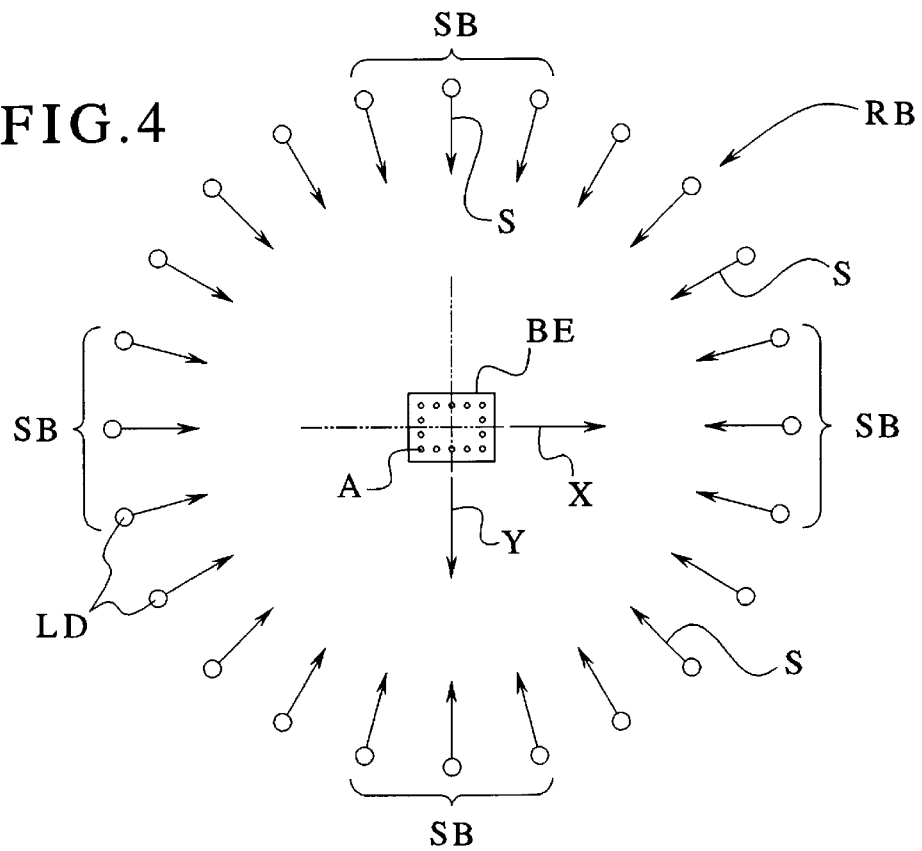
FIG. 4 depicts a second modification of the schematic diagram shown in FIG. 2.

According to FIG. 4, the effect of the ring light illumination RB desired for the suppression of unwanted structures can also be achieved in that the light-emitting diodes LD in the segment regions SB corresponding to the angular segments WS are not activated. This arrangement has the advantage that the light-emitting diodes LD in the segment regions SB can be added in for increasing intensity given components BE with less strongly pronounced unwanted structures.

Figure 5:
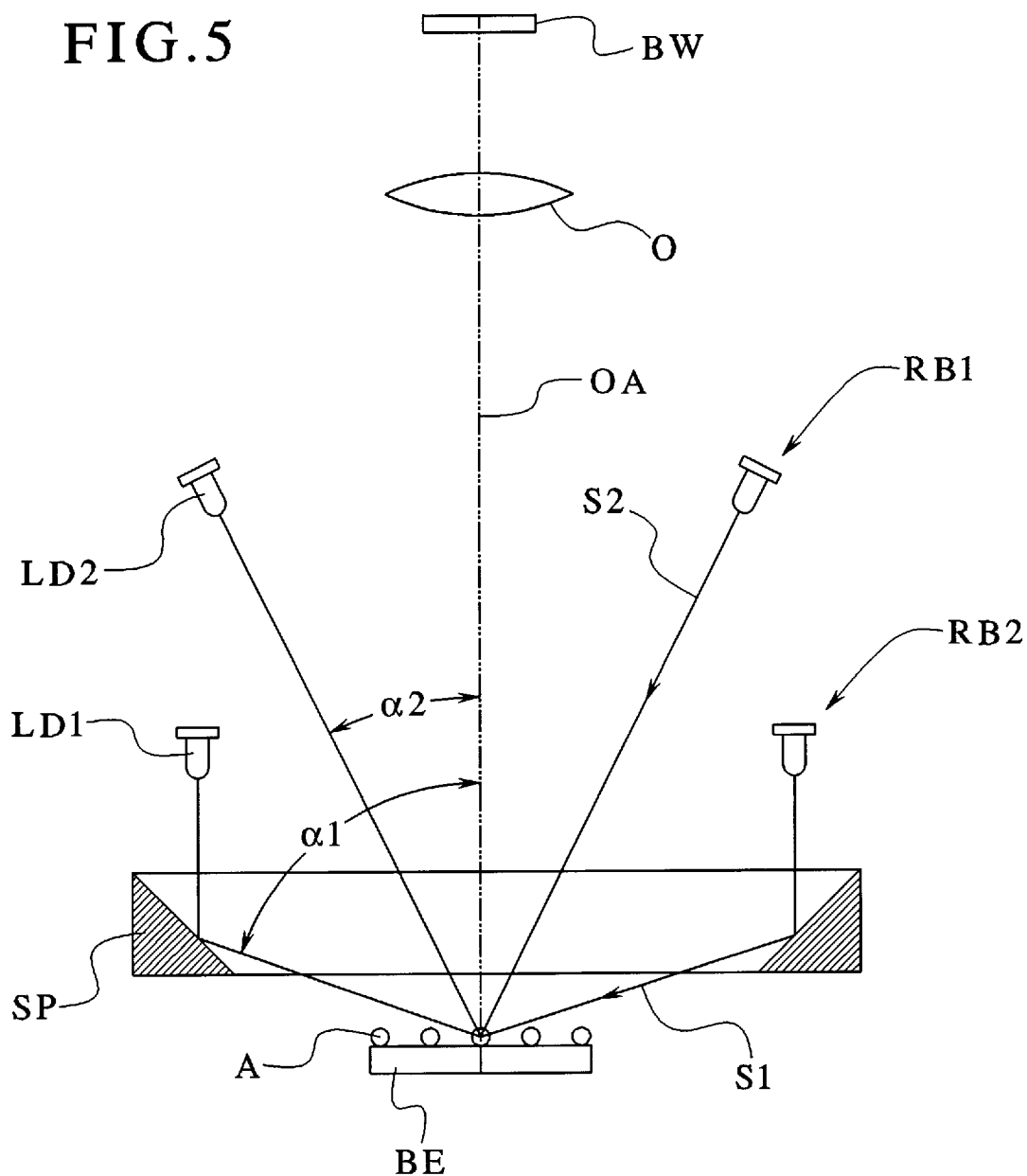
FIG. 5 depicts a device for recognizing the position of the terminals of components, shown in longitudinal section.

In a highly simplified schematic illustration, FIG. 5 shows a device for recognizing the position of the terminals A of components BE in longitudinal section. With, for example, the suction pipette (not shown in greater detail in FIG. 5) of an equipping head, the components BE are thereby brought into the position required for recognizing the position of the terminals A. In this position, the components BE are centrally aligned relative to the optical axis OA of an objective that images the terminals A onto the light-sensitive surface of an image transducer BW. For example, the image transducer BW is a matter of a CCD camera of the type Sony XC75C with 484 effective rows and 746 effective columns.

A first ring light illumination RB1 and a second ring light illumination RB2, which can both be separately activated and deactivated, are provided for illuminating the surface of a component BE.

The first ring light illumination RB1 comprises a plurality of light-emitting diodes LD1 that, according to the principle shown in FIG. 4, are arranged on a circle concentric with the optical axis OA. The rays S1 emanating from the light-emitting diodes are steered onto the surface of the component BE via an annular mirror SP that is aligned coaxially with the optical axis OA, whereby the illumination angle measured toward the optical axis OA is a $\alpha 1 = 60°$.

The first ring light illumination RB1 is utilized for the illumination of components BE with highly pronounced unwanted structures, whereby—according to the pattern shown in FIG. 4—segment regions SB of ±10° around the principal directions X and Y are not activated. The segment regions SB, however, can be activated as auxiliary illumination for increasing the intensity given components BE with less highly pronounced unwanted structures.

Figure 3:
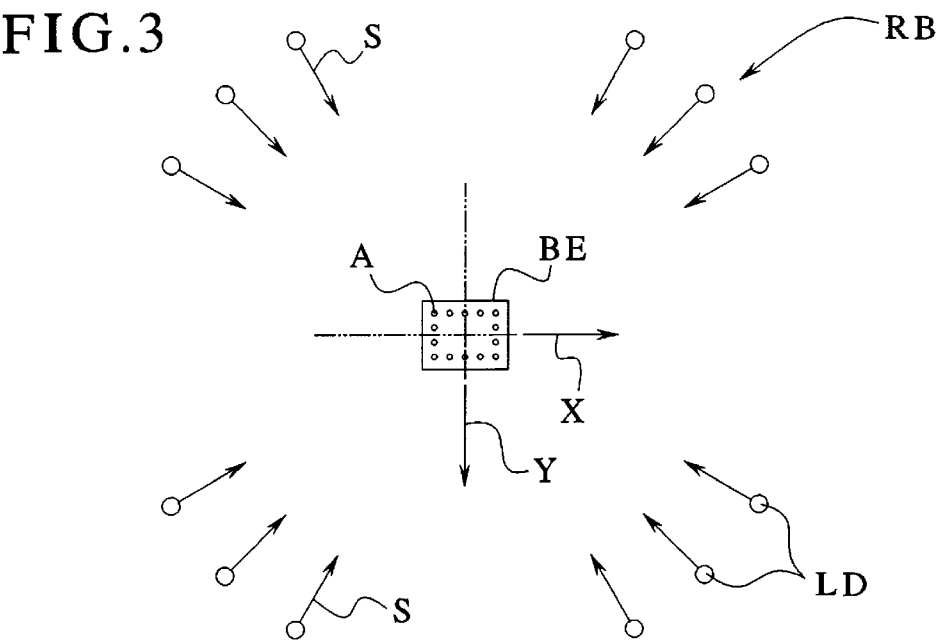
FIG. 3 depicts a first modification of the schematic diagram shown in FIG. 2.

The second ring light illumination RB2 comprises a plurality of light-emitting diodes LD2 that—according to the principle shown in FIG. 3—are arranged on a circle concentric with the optical axis OA. The rays S emanating from the light-emitting diodes LD2 are directed directly onto the surface of the component BE, whereby the illumination angle measured toward the optical axis OA is $\alpha 2 = 30°$.

The second ring light illumination RB2 is utilized for the high-intensity illumination of components BE with weak unwanted structures, whereby—according to the pattern shown in FIG. 3—angular segments of ±14° around the principal directions X and Y are excluded from the illumination for suppressing unwanted structures.

For example, light-emitting diodes HLMP8103 Type T that emit red light with a wavelength of 637 nm are utilized for the first ring light illumination RB1 and the second ring light illumination RB2.

The device shown in FIG. 5 is utilized in automatic equipping units for components vision systems. In particular, it is suitable for reliably recognizing the position of the spherical terminals of components.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A device for recognizing a position of terminals of components, comprising:

the components having optically disturbing surface structures at terminal sides thereof that proceed in two principal directions residing perpendicular to one another that proceed parallel to lateral edges of a component;

the components being placeable in an active region of the device:

an image transducer having an objective and at least one segmented ring light illumination:

the objective having an optical axis that proceeds at least approximately through a center of the ring light illumination:

the objective and the ring light illumination arranged above a location provided for the components; and the respective component being placeable relative to the ring light illumination at least approximately centrally in an angular position wherein rays of the ring light illumination upon exclusion of angular segments lying in a region of the principal directions, are directed obliquely onto the surface of the components from all sides of the components.

2. The device according to claim 1, the excluded angular segments of the ring light illumination lie in an angular range deviating −15° through +15° from the principal directions.

3. The device according to claim 1, the excluded angular segments of the ring light illumination lie in an angular range deviating approximately ±10° from the principal directions.

4. The device according to claim 1, wherein the rays of the segmented ring light illumination are directed onto the surface of the components at an illumination angle of 45 to 90° relative to an optical axis of the objective.

5. The device according to claim 4, wherein the segmented ring light illumination, comprises:

light-emitting diodes that, upon exclusion of the angular segments, are arranged by sectors on a circle or polygon coaxial with the optical axis of the objective; and a segmented ring light illumination having an annular or polygonal mirror arranged coaxially with the optical axis of the objective that steers rays emitted by the light-emitting diodes obliquely onto the surface of the components.

6. The device according to claim 1, wherein the rays of the segmented ring light illumination are directed onto the surface of the components at an illumination angle of 55 to 65° relative to an optical axis of the objective.

7. The device according to claim 6, wherein the segmented ring light illumination, comprises:

light-emitting diodes that, upon exclusion of the angular segments, are arranged by sectors on a circle or polygon coaxial with the optical axis of the objective; and a segmented ring light illumination having an annular or polygonal mirror arranged coaxially with the optical axis of the objective that steers rays emitted by the light-emitting diodes obliquely onto the surface of the components.

8. The device according to claim 1, wherein the rays of the segmented ring light illumination are directed onto the surface of the components at an illumination angle of approximately 60° relative to an optical axis of the objective.

9. The device according to claim 6, wherein the segmented ring light illumination comprises:

light-emitting diodes that, upon exclusion of the angular segments, are arranged by sectors on a circle or polygon coaxial with the optical axis of the objective; and a segmented ring light illumination having an annular or polygonal mirror arranged coaxially with the optical axis of the objective that steers rays emitted by the light-emitting diodes obliquely onto the surface of the components.

10. The device according to claim 1, wherein the device further comprises a second segmented ring light illumination that is separately activatable, the second segmented ring light illumination having rays incident onto the surface of the components at an illumination angle of 15 to 45° relative to the optical axis of the objective.

11. A device for recognizing a position of terminals of components, comprising:

the components having optically disturbing surface structures at terminal sides thereof that proceed in two principal directions residing perpendicular to one another that proceed parallel to lateral edges of a component:

the components being placeable in an active region of the device:

an image transducer having an objective and at least one segmented ring light illumination:

the objective having an optical axis that proceeds at least approximately through a center of the ring light illumination:

the objective and the ring light illumination arranged above a location provided for the components: and the respective component being placeable relative to the ring light illumination at least approximately centrally in an angular position wherein rays of the ring light illumination upon exclusion of angular segments lying in a region of the principal directions, are directed obliquely onto the surface of the components from all sides of the components, a second segmented ring light illumination that is separately activatable, the second segmented ring light illumination having rays incident onto the surface of the components at an illumination angle of 25 to 35° relative to the optical axis of the objective.

12. The device according to claim 11, wherein the second segmented ring light illumination has light-emitting diodes that, upon exclusion of the angular segments, are arranged by sectors on a circle or polygon coaxial with the optical axis of the objective.

13. A device for recognizing a position of terminals of components, comprising:

the components having optically disturbing surface structures at terminal sides thereof that proceed in two principal directions residing perpendicular to one another that proceed parallel to lateral edges of a component:

the components being placeable in an active region of the device:

an image transducer having an objective and at least one segmented ring light illumination:

the objective having an optical axis that proceeds at least approximately through a center of the ring light illumination:

the objective and the ring light illumination arranged above a location provided for the components: and the respective component being placeable relative to the ring light illumination at least approximately centrally in an angular position wherein rays of the ring light illumination upon exclusion of angular segments lying in a region of the principal directions, are directed obliquely onto the surface of the components from all sides of the components, a second segmented ring light illumination that is separately activatable, the second segmented ring light illumination having rays are incident onto the surface of the components at an illumination angle of approximately 30° relative to the optical axis of the objective.

14. The device according to claim 10, wherein the second segmented ring light illumination has light-emitting diodes that, upon exclusion of the angular segments, are arranged by sectors on a circle or polygon coaxial with the optical axis of the objective.

15. A device for recognizing a position of terminals of components, comprising:

the components having optically disturbing surface structures at terminal sides thereof that proceed in two principal directions residing perpendicular to one another that proceed parallel to lateral edges of a component:

the components being placeable in an active region of the device:

an image transducer having an objective and at least one segmented ring light illumination:

the objective having an optical axis that proceeds at least approximately through a center of the ring light illumination:

the objective and the ring light illumination arranged above a location provided for the component: and the respective component being placeable relative to the ring light illumination at least approximately centrally in an ancular position wherein rays of the ring light illumination upon exclusion of angular segments lying in a region of the principal directions, are directed obliquely onto the surface of the components from all sides of the components, a second segmented ring light illumination that is separately activatable, the second segmented ring light illumination having rays incident onto the surface of the components at an illumination angle of 15 to 45° relative to the optical axis of the objective:

the second segmented ring light illumination having light-emitting diodes that, upon exclusion of the angular segments, are arranged by sectors on a circle or polygon coaxial with the optical axis of the objective.

* * * * *